United States Patent
Garde et al.

(10) Patent No.: US 10,537,700 B2
(45) Date of Patent: Jan. 21, 2020

(54) SYSTEM AND METHOD FOR SUCTIONING FOR SECRETION REMOVAL FROM THE AIRWAY OF A MECHANICALLY VENTILATED SUBJECT

(75) Inventors: Smita Garde, Irvine, CA (US); Gardner Kimm, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1828 days.

(21) Appl. No.: 13/501,765

(22) PCT Filed: Oct. 11, 2010

(86) PCT No.: PCT/IB2010/054596
§ 371 (c)(1),
(2), (4) Date: Apr. 13, 2012

(87) PCT Pub. No.: WO2011/045735
PCT Pub. Date: Apr. 21, 2011

(65) Prior Publication Data
US 2012/0199127 A1    Aug. 9, 2012

Related U.S. Application Data

(60) Provisional application No. 61/252,231, filed on Oct. 16, 2009.

(51) Int. Cl.
*A61M 16/16* (2006.01)
*A61M 16/00* (2006.01)

(52) U.S. Cl.
CPC ...... *A61M 16/161* (2014.02); *A61M 16/0009* (2014.02); *A61M 16/024* (2017.08);
(Continued)

(58) Field of Classification Search
CPC .............. A61M 16/00; A61M 16/0003; A61M 16/105; A61M 16/043; A61M 16/0486;
(Continued)

(56) References Cited

U.S. PATENT DOCUMENTS

| 4,821,709 A | * | 4/1989 | Jensen | ............... A61M 16/0096 128/204.21 |
| 5,345,930 A | | 9/1994 | Cardinal | |

(Continued)

FOREIGN PATENT DOCUMENTS

| WO | 2003045486 A1 | 6/2003 |
| WO | 2004064885 A2 | 8/2004 |

(Continued)

*Primary Examiner* — Samchuan C Yao
*Assistant Examiner* — Ned T Heffner
(74) *Attorney, Agent, or Firm* — Michael W. Haas

(57) ABSTRACT

Secretions that have accumulated at or near an airway of a subject (12) as the subject (12) is being mechanically ventilated are removed by suctioning. Before, during, and/or after the removal of the secretions, steps are taken to mitigated the impact of the suctioning used for secretion removal on the subject (12). As such, the timing of suction used to remove secretions may be influenced or controlled, ventilation of the subject (12) during suction may be adjusted, ventilation of the subject (12) prior to secretion removal may be adjusted to prepare the lungs of the subject (12) for secretion removal, ventilation of the subject (12) subsequent to suction for secretion removal may be adjusted, and/or other techniques for reducing the impact of suctioning for secretion removal on the subject (12) may be implemented.

18 Claims, 5 Drawing Sheets

(52) U.S. Cl.
CPC ............ *A61M 2016/0021* (2013.01); *A61M 2016/0036* (2013.01); *A61M 2202/0208* (2013.01); *A61M 2205/18* (2013.01); *A61M 2205/332* (2013.01); *A61M 2205/3368* (2013.01); *A61M 2205/3375* (2013.01); *A61M 2205/3584* (2013.01); *A61M 2205/3592* (2013.01); *A61M 2205/505* (2013.01); *A61M 2205/52* (2013.01)

(58) Field of Classification Search
CPC .. A61M 2016/0021; A61M 2016/0027; A61M 2016/0036; A61M 2016/0039; A61M 16/0051; A61M 16/04; A61M 2016/039; A62B 7/00; A62B 9/006; A61B 9/006; A61B 9/00
See application file for complete search history.

(56) References Cited

U.S. PATENT DOCUMENTS

| | | | |
|---|---|---|---|
| 5,400,778 | A | 3/1995 | Jonson |
| 5,752,921 | A * | 5/1998 | Orr ........................ 600/533 |
| 2005/0039749 | A1 | 2/2005 | Emerson |
| 2007/0186928 | A1* | 8/2007 | Be'Eri ................ 128/204.18 |
| 2007/0199566 | A1* | 8/2007 | Be'eri ................. 128/204.23 |
| 2009/0126731 | A1 | 5/2009 | Dunsmore et al. |
| 2009/0145428 | A1 | 6/2009 | Sward et al. |

FOREIGN PATENT DOCUMENTS

| | | |
|---|---|---|
| WO | 2007054829 A2 | 5/2007 |
| WO | 2007066332 A2 | 6/2007 |

* cited by examiner

SYSTEM AND METHOD FOR SUCTIONING FOR SECRETION REMOVAL FROM THE AIRWAY OF A MECHANICALLY VENTILATED SUBJECT

BACKGROUND OF THE INVENTION

1. Field of the Invention

The invention relates to removal of secretions from the airway of a mechanically ventilated subject.

2. Description of the Related Art

Systems for removing secretions from the airway of a subject being mechanically ventilated are known. Generally, such systems include a suction catheter that is inserted into an interface appliance that interfaces with the airway of the subject. Suction is applied to the flow path formed by the interface appliance and the airway of the subject through the suction catheter to remove secretions.

Typically, such systems operate separately and discretely from a ventilation system that is mechanically ventilating the subject. As such, the application of suction to the airway of the subject is made without reference to the ventilation system and/or the ventilation being provided to the subject. Similarly, the ventilation system usually does not alter or adjust ventilation of the subject in cooperation with the application of suction to remove secretions.

SUMMARY OF THE INVENTION

One aspect of the invention relates to a ventilation system configured to generate a pressurized flow of breathable gas that is delivered to the airway of a subject to mechanically ventilate the subject. In one embodiment, the ventilation system comprises a pressure generator, a sensor, and a processor. The pressure generator is configured to generate a pressurized flow of breathable gas for delivery to an airway of a subject, the pressurized flow of breathable gas having one or more controllable gas parameters. The sensor is configured to generate an output signal conveying information related to one or gas parameters at or near the airway of the subject. The processor is configured to a suction timing module, the suction timing module being configured to generate a trigger signal indicating that suction through a suction catheter positioned at or near the airway of the subject to remove secretions should be initiated, wherein the trigger signal is generated based on the output signal generated by the sensor.

Another aspect of the invention relates to a method of generating a pressurized flow of breathable gas that is delivered to the airway of a subject to mechanically ventilate the subject. In one embodiment, the method comprises generating a pressurized flow of breathable gas for delivery to an airway of a subject, the pressurized flow of breathable gas having one or more controllable gas parameters; generating an output signal conveying information related to one or gas parameters at or near the airway of the subject; determining, based on the output signal, that suction through a suction catheter positioned at or near the airway of the subject to remove secretions should be initiated; and generating, responsive to the determination that suction through the suction catheter should be initiated, a trigger signal indicating that suction through the suction catheter should be initiated.

Yet another aspect of the invention relates to a system configured to generate a pressurized flow of breathable gas that is delivered to the airway of a subject to mechanically ventilate the subject. In one embodiment, the system comprises means for generating a pressurized flow of breathable gas for delivery to an airway of a subject, the pressurized flow of breathable gas having one or more controllable gas parameters; means for generating an output signal conveying information related to one or gas parameters at or near the airway of the subject; means for determining, based on the output signal, that suction through a suction catheter positioned at or near the airway of the subject to remove secretions should be initiated; and means for generating, responsive to the determination that suction through the suction catheter should be initiated, a trigger signal indicating that suction through the suction catheter should be initiated.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
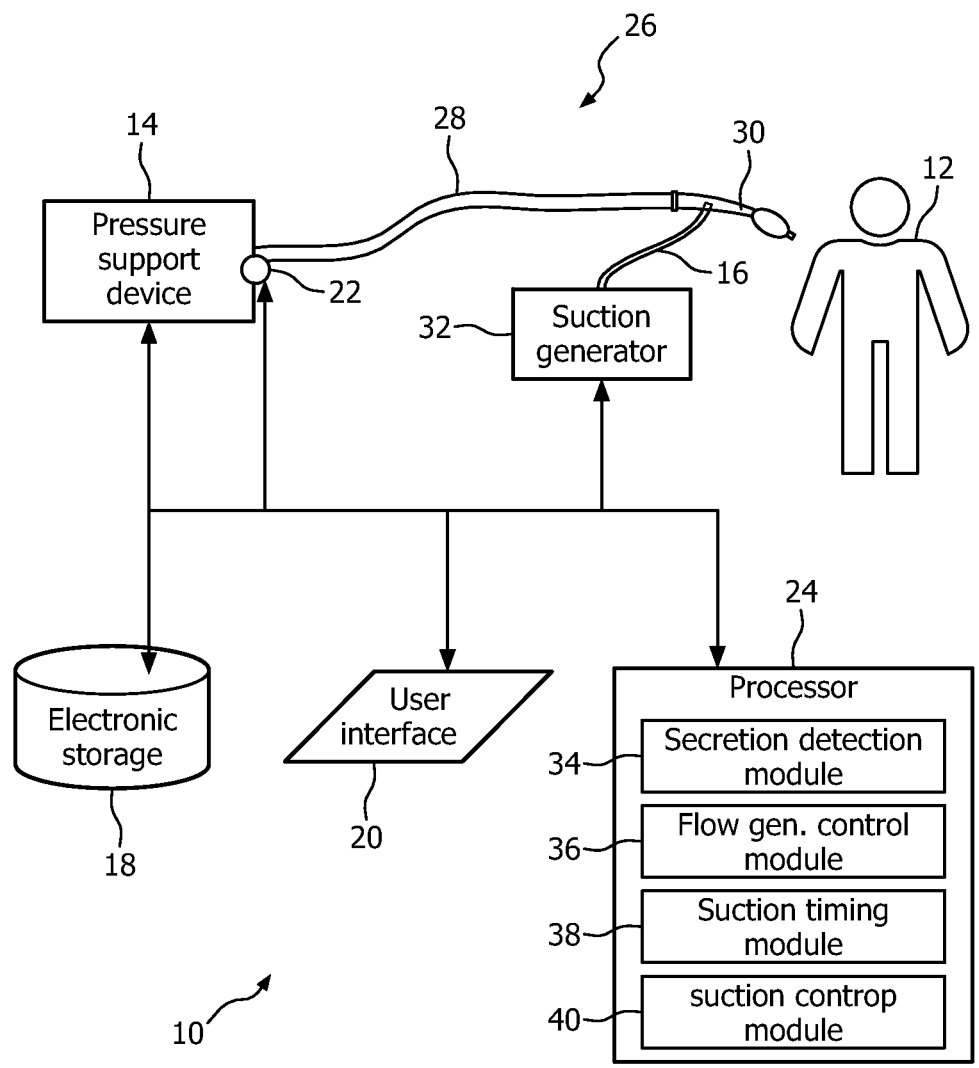
FIG. 1 illustrates a system configured to remove secretions that have accumulated at or near the airway of a subject, according to one or more embodiments of the invention.

FIG. 1 illustrates a system 10 configured to remove secretions that have accumulated at or near an airway of a subject 12 as subject 12 is being mechanically ventilated. The system is configured to reduce the impact of secretion removal on subject 12. As such, system 10 may influence or control the timing of suction used to remove secretions, compensating for the impact of suction used to remove secretions by adjusting ventilation of the subject 12 during suction, adjusting ventilation of subject 12 prior to secretion removal to prepare the lungs of subject 12 for secretion removal, adjusting ventilation of subject 12 subsequent to secretion removal, and/or other implement other techniques for reducing the impact of secretion removal on subject 12.

This may enhance the health of subject 12 (e.g., by preserving lung capacity, etc.), the comfort of subject 12, and/or may provided other enhancements. In one embodiment, system 10 includes one or more of a pressure generator 14, a suction catheter 16, electronic storage 18, a user interface 20, one or more sensors 22, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow rate, pressure, volume, humidity, temperature, gas composition, breath rate, tidal volume, peak flow, inhalation timing, exhalation timing, etc.) for therapeutic purposes, or for other purposes. By way of non-limiting example, pressure generator 14 may be configured to control the pressure, the flow rate, the composition, the humidity, the temperature, the acceleration, the velocity, the breath rate, the tidal volume, the peak flow, inhalation timing, exhalation timing, rise time, flow waveform patterns, triggering and cycling sensitivity, and/or other parameters of the pressurized flow of breathable gas generated. In one embodiment, pressure generator 14 is configured to generate the pressurized flow of breathable gas such that delivery of the pressurized flow of breathable gas to the airway of subject 12 mechanically ventilates subject 12. For instance, pressure generator 14 may include a ventilator, an in-exsufflation device, and/or other devices configured to mechanically ventilate subject 12.

The pressurized flow of breathable gas is delivered to the airway of subject 12 via a subject interface 26. Subject interface 26 is configured to communicate the pressurized flow of breathable gas generated by pressure support device 14 to the airway of subject 12. As such, subject interface 26 includes a conduit 28 and an interface appliance 30. Conduit conveys the pressurized flow of breathable gas to interface appliance 30, and interface appliance 30 delivers the pressurized flow of breathable gas to the airway of subject 12. Some examples of interface appliance 30 may include, for example, an endotracheal tube, a tracheotomy tube, or other interface appliances configured to communicate a flow of gas with an airway of a subject to mechanically ventilate the subject. The present invention is not limited to these examples, and contemplates delivery of the pressurized flow of breathable gas to subject 12 using any subject interface.

Although pressure generator 14 and subject interface 26 are illustrated in FIG. 1 as a single-limb system, this is for illustrative purposes. It will be appreciated that to mechanically ventilate subject 12, subject interface 26 also includes a second limb that enables gas to be exhausted away from interface appliance 30. In such an embodiment, pressure generator 14 may include a positive pressure generator providing the functionality attributed to pressure generator 14 above that is connected to a first limb of subject interface 26, while the second limb of subject interface 26 facilitates exhalation by subject 12.

During mechanical ventilation of subject 12, subject 12 will typically be unable to clear secretions from the airway manually. As such, suction catheter 16 can be inserted into the airway of subject 12 to remove the secretions by suction. In one embodiment, suction catheter 16 is configured to be inserted through an opening in interface appliance 30 (e.g., an adaptor connected to an endotracheal tube) and into the flow path that includes interface appliance 30 and the airway of subject 12. Through the inserted end of suction catheter 16, secretions are suctioned out of the flow path.

To provide suction at the inserted end of suction catheter 16, the opposite end of suction catheter 16 may be in fluid communication with a suction generator 32. The suction generator 32 may be configured to controllably apply a negative pressure to suction catheter 16, and may be configured to receive, exhaust, and/or dispose of secretions suctioned from the flow path formed by interface appliance 30 and the airway of subject 12. In one embodiment, suction generator 32 and pressure generator 14 are included in a common device or apparatus. In one embodiment, suction generator 32 and pressure generator 14 are separate devices. The separate devices may be communicatively linked, and/or they may be operated separately in a coordinated manner by a user (e.g., a caregiver, a researcher, etc.).

In one embodiment, electronic storage 18 comprises electronic storage media that electronically stores information. The electronically storage media of electronic storage 18 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 18 may store software algorithms, information determined by processor 24, information received via user interface 20, and/or other information that enables system 10 to function properly. Electronic storage 18 may be (in whole or in part) a separate component within system 10, or electronic storage 18 may be provided (in whole or in part) integrally with one or more other components of system 10 (e.g., pressure generator 14, suction generator 32, user interface 20, processor 24, etc.).

User interface 20 is configured to provide an interface between system 10 and a user (e.g., subject 12, a caregiver, a researcher, etc.) through which the user may provide information to and receive information from system 10. This enables data, results, and/or instructions and any other communicable items, collectively referred to as "information," to be communicated between the user and one or more of pressure generator 14, electronic storage 18, and/or processor 24. Examples of interface devices suitable for inclusion in user interface 20 include a keypad, buttons, switches, a keyboard, knobs, levers, a display screen, a touch screen, speakers, a microphone, an indicator light, an audible alarm, a printer, and/or other interface devices. In one embodiment, user interface 20 includes at least one interface that is provided integrally with pressure generator 14. In one embodiment, user interface 20 includes a plurality of separate interfaces. For example, user interface 20 may include at least one interface that is provided integrally with pressure generator 14 and at least one interface that is provided with suction generator 32.

It is to be understood that other communication techniques, either hard-wired or wireless, are also contemplated by the present invention as user interface 20. For example, the present invention contemplates that user interface 20 may be integrated with a removable storage interface provided by electronic storage 18. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 20 include, but are not limited to, an RS-232 port, RF link, an IR link, modem (telephone, cable or other). In short, any technique for communicating information with system 10 is contemplated by the present invention as user interface 20.

One or more sensors 22 are configured to generate one or more output signals conveying information related to one or more parameters of the pressurized flow of breathable gas. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. The sensors 22 may include one or more sensors that measure such parameters directly (e.g., through fluid communication with the pressurized flow of breathable gas at pressure generator 14 or in subject interface 26). The sensors 22 may include one or more sensors that generate output signals related to one or more parameters of the pressurized flow of breathable gas indirectly. For example, one or more of sensors 22 may generate an output based on an operating parameter of pressure generator 14 (e.g., a valve driver current, voltage, rotational velocity, and/or other operating parameters), and/or other sensors. Although sensors 22 are illustrated at a single location at or adjacent to pressure generator 14, this is not intended to be limiting. The sensors 22 may include sensors disposed in a plurality of locations, such as for example, within pressure generator 14, within (or in communication with) conduit 28, within (or in communication with) interface appliance 30, and/or other locations.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination (e.g., at least one processor integral with pressure generator 14 and at least one processor integral with suction generator 32).

As is shown in FIG. 1, processor 24 may be configured to execute one or more computer program modules. The one or more computer program modules may include one or more of a secretion detection module 34, a flow generator control module 36, a suction timing module 38, a suction control module 40, and/or other modules. Processor 24 may be configured to execute modules 34, 36, 38, and/or 40 by software; hardware; firmware; some combination of software, hardware, and/or firmware; and/or other mechanisms for configuring processing capabilities on processor 24.

It should be appreciated that although modules 34, 36, 38, and 40 are illustrated in FIG. 1 as being co-located within a single processing unit, in implementations in which processor 24 includes multiple processing units, one or more of modules 34, 36, 38, and/or 40 may be located remotely from the other modules. The description of the functionality provided by the different modules 34, 36, 38, and/or 40 described below is for illustrative purposes, and is not intended to be limiting, as any of modules 34, 36, 38, and/or 40 may provide more or less functionality than is described. For example, one or more of modules 34, 36, 38, and/or 40 may be eliminated, and some or all of its functionality may be provided by other ones of modules 34, 36, 38, and/or 40. As another example, processor 24 may be configured to execute one or more additional modules that may perform some or all of the functionality attributed below to one of modules 34, 36, 38, and/or 40.

The secretion detection module 34 is configured to detect secretions present in the flow path formed by interface appliance 30 and the airway of subject 12. The secretion detection module 34 detects secretions based on the output signals generated by sensors 22. For example, in one embodiment, secretion detection module 34 determines a peak inspiratory pressure of subject 12 based on the output signals generated by sensors 22. As secretions collect in the airway of subject 12, the peak inspiratory pressure will tend to increase as the secretions effectively reduce flow area through the flow path formed by interface appliance 30 and the airway of subject 12. The secretion detection module 34 may detect secretions present in the flow path formed by interface appliance 30 and the airway of subject 12 based on an increase in peak inspiratory pressure. For example, if the peak inspiratory pressure rises above a predetermined threshold, secretion detection module 34 may determine that secretions within the flow path formed by interface appliance 30 and the airway of subject 12 need to be suctioned.

Upon detecting secretions in the flow path formed by interface appliance 30 and the airway of subject 12 requiring removal by suction, secretion detection module 34 generates a trigger signal indicating that a secretion removal routine should be initiated. The secretion removal routine may include one or more of a pre-suction sub-routine, a suction sub-routine, and/or a post-section sub-routine. The secretion removal routine may include operations that are performed automatically and/or operations performed manually (e.g., by a caregiver). The operations performed manually may be initiated based on cues generated by system 10 (e.g., by user interface 20) for a user. As used herein, "cues" may include any indications generated by system 10 that are perceptible by a user. For example, the cues may include one or more of an auditory cue, a visual cue, a tactile cue, and/or other cues. As such, the trigger signal generated by interface appliance 30 may automatically initiate one or more operations associated with the secretion removal routine, and/or may result in the generation of a cue by system 10 that conveys to a user that one or more operations associated with the secretion removal routine should be performed.

The flow generator control module 36 is configured to control pressure generator 14 to selectively adjust one or more controllable gas parameters of the pressurized flow of breathable gas. During typical operation, flow generator control module 36 controls pressure generator 14 to adjust the one or more controllable gas parameters of the pressurized flow of breathable gas to facilitate mechanical ventilation of subject 12 that is comfortable to subject 12, that preserves lung capacity of subject 12, and/or provides other benefits to subject 12. The flow generator control module 36 may control pressure generator 14 in accordance with one or more different types of ventilation modes. By way of non-limiting example, the ventilation modes may include one or more of volume control, pressure control, pressure support, synchronized intermittent mandatory ventilation, and/or other ventilation modes. The mode implemented to mechanically ventilate subject 12 may be selected by a user (e.g., a caregiver, etc.) via user interface 20, may be dictated by measure respiratory functionality of subject 12, and/or based on other parameters.

In one embodiment, flow generator control module 36 controls pressure generator 14 to facilitate removal of secretions from the flow path formed by interface appliance 30 and the airway of subject 12 during the secretion removal routine, and/or to reduce the impact of the secretion removal routine on subject 12. This may include one or more of controlling pressure generator 14 the pre-suction sub-routine, controlling pressure generator 14 during the suction sub-routine, and/or controlling pressure generator 14 during the post-suction sub-routine.

During the pre-suction sub-routine, flow generator control module 36 controls pressure generator 14 to adjust the one or more controllable gas parameters of the pressurized flow of breathable gas to mitigate adverse effects of suctioning, and/or to improve clearance of secretions by suctioning. By way of non-limiting example, during the pre-suction sub-routine, the oxygen content of the pressurized flow of breathable gas may be elevated, the humidity of the pressurized flow of breathable gas may be elevated, the pressure and/or flow of the pressurized flow of breathable gas may be adjusted to insufflate subject 12, adjust positive end expiratory pressure ("PEEP"),and/or other gas parameters may be adjusted. In one embodiment, control over pressure generator 14 by flow generator control module 36 during the pre-suction sub-routine is initiated automatically based on the trigger signal generated by secretion detection module 34. In one embodiment, the trigger signal generated by secretion detection module 34 results in the generation of a cue to the user that the secretion removal routine should be commenced. In response to this cue, the user may input one or more control commands (e.g., via user interface 20) that instruct flow generator control module 36 to control pressure generator 14 to automatically adjust the one or more controllable gas parameters of the pressurized flow of breathable gas in accordance with the pre-suction sub-routine.

In one embodiment, the adjustments made to the one or more controllable gas parameters of the pressurized flow of breathable gas effected by flow generator control module 36 during the pre-suction sub-routine are configurable by a user (e.g., a caregiver, an administrator, a decision maker, etc.). For example, different entities, such as hospitals, clinics, universities, institutions, and/or other entities, may have different guidelines for performing secretion removal. The system 10 may be configured such that via user interface 20, a user may configure the adjustments made to the pressurized flow of breathable gas by flow generator control module 36 during the pre-suction sub-routine to customize the pre-suction sub-routine with respect to the guidelines of a particular entity. By way of non-limiting example, the user may configure one or more of a start time, an end time, an adjustment amount, a frequency, a pulse-width, and/or other aspects of the adjustments made to the one or more controllable gas parameters of the pressurized flow of breathable gas.

Upon completion of the pre-suction sub-routine, system 10 may proceed to the suction sub-routine, in which suction is applied to the flow path formed by interface appliance 30 and the airway of subject 12 to remove secretions. The system 10 may proceed to the suction sub-routine automatically. This may be based on the trigger signal generated by flow generator control module 36, or upon completion of the pre-suction sub-routine. In one embodiment system 10 proceeds to the suction sub-routine based on a user control input (e.g., received via user interface 20). The user may be prompted to input the user control input by the generation of a cue. The cue may be generated based on the trigger signal generated by flow generator control module 36, or upon completion of the pre-suction sub-routine.

As was mentioned above, during the suction sub-routine, suction is applied by the flow path formed by interface appliance 30 and the airway of subject 12 via an end of suction catheter 16 that is inserted into interface appliance 30 and/or the airway of subject 12. The application of suction within flow path formed by interface appliance 30 and the airway of subject 12 has a tendency to lower the pressure within the airway of subject 12. This reduction in pressure may result in loss of lung capacity, oxygen desaturation, discomfort and pain to subject 12, ventilator malfunction, and/or have other impacts. During the suction sub-routine, flow generator control module 36 may control pressure generator 14 to adjust one or more parameters of the controllable gas parameters of the pressurized flow of breathable gas to reduce variation in one or more gas parameters (e.g., pressure, flow, volume, etc.) at or near the airway of subject 12.

In one embodiment, such adjustment includes maintaining triggering and cycling dictated by a ventilation mode as suctioning is ongoing. In one embodiment, adjustments made by flow generator control module 36 during the suction sub-routine include keeping one or more gas parameters at or near the airway of subject 12 from breaching predetermined thresholds. For example, flow generator control module 36 may adjust the pressurized flow of breathable gas to maintain pressure at or near the airway of subject 12 above a pressure threshold. In one embodiment, adjustments made by flow generator control module 36 during the suction sub-routine include incorporating bias flow to compensate for the suctioning. In one embodiment, adjustments made by flow generator control module 36 during the suction sub-routine include increasing tidal volume during inspiration. In one embodiment, adjustments made by flow generator control module 36 during the suction sub-routine include adjusting or switching ventilation modes. For example, a synchronized intermittent mandatory ventilation ("SIMV") mode, may be avoided during the suction sub-routine, as SIMV modes may generate hyperinflated breaths when used in conjunction with suctioning.

In one embodiment, the adjustments made to the one or more controllable gas parameters of the pressurized flow of breathable gas effected by flow generator control module 36 during the suction sub-routine are configurable by a user (e.g., a caregiver, an administrator, a decision maker, etc.). For example, different entities, such as hospitals, clinics, universities, institutions, and/or other entities, may have different guidelines for performing secretion removal. The system 10 may be configured such that via user interface 20, a user may configure the adjustments made to the pressurized flow of breathable gas by flow generator control module 36 during the suction sub-routine to customize the suction sub-routine with respect to the guidelines of a particular entity. By way of non-limiting example, the user may configure one or more of a start time, an end time, an adjustment amount, a frequency, a pulse-width, a ventilation mode, and/or other aspects of the adjustments made to the one or more controllable gas parameters of the pressurized flow of breathable gas Upon completion of the suction sub-routine, system 10 may proceed to the post-suction sub-routine, in which one or more steps are taken to mitigate the impact of the secretion removal routine on subject 12. The system 10 may proceed to the post-suction sub-routine automatically upon completion of the suction sub-routine. In one embodiment system 10 proceeds to the post-suction sub-routine based on a user control input (e.g., received via user interface 20). The user may be prompted to input the user control input by the generation of a cue. The cue may be generated based on completion of the suction sub-routine.

During the post-suction sub-routine, flow generator control module 36 controls pressure generator 14 to adjust one or more gas parameters of the pressurized flow of breathable gas to mitigate the impact of the secretion removal routine on subject 12. These adjustments may include providing an elevated level of oxygen content in the pressurized flow of breathable gas, performance of lung recruitment maneuvers, and/or other adjustments tending to mitigate the impact of the secretion removal routine on subject 12.

The suction timing module 38 is configured to determine the timing during the suction sub-routine at which suction through suction catheter 16 should be administered. If the suction applied to the flow path formed by interface appliance 30 and the airway of subject 12 during the suction sub-routine causes negative pressure in the airway of subject 12, lung capacity may be compromised to some extent. As such, suction timing module 38 is configured to monitor the timing of the ventilation provided to subject 12, and to determine the timing at which suction to the flow path formed by interface appliance 30 and the airway of subject 12 can be administered without resulting in negative pressure in the lungs of subject 12 (or at least increasing the minimum pressure and/or reducing the amount of time a negative pressure exists). The timing of administration of the suction may include one or more of a start time of an application of suction, an end time of an application of suction, a duration of an application of suction, and/or other timings related to the administration of the suction during the suction sub-routine. The suction timing module 38 may determine the timing at which suction through suction catheter 16 should be administered based on the output signals generated by sensors 22 and/or based on one or more sensors that monitor the operation of pressure generator 14.

Upon determining the timing at which the suction should be administered, suction timing module 38 generates a trigger signal at the appropriate time, the trigger signal indicating that the suction should be administered. The trigger signal may be implemented by system 10 to automatically initiate suction (e.g., as described below), and/or system 10 may generate one or more cues to a user to administer suction (e.g., to begin suction, to end suction, etc.) based on the trigger signal.

Figure 2:
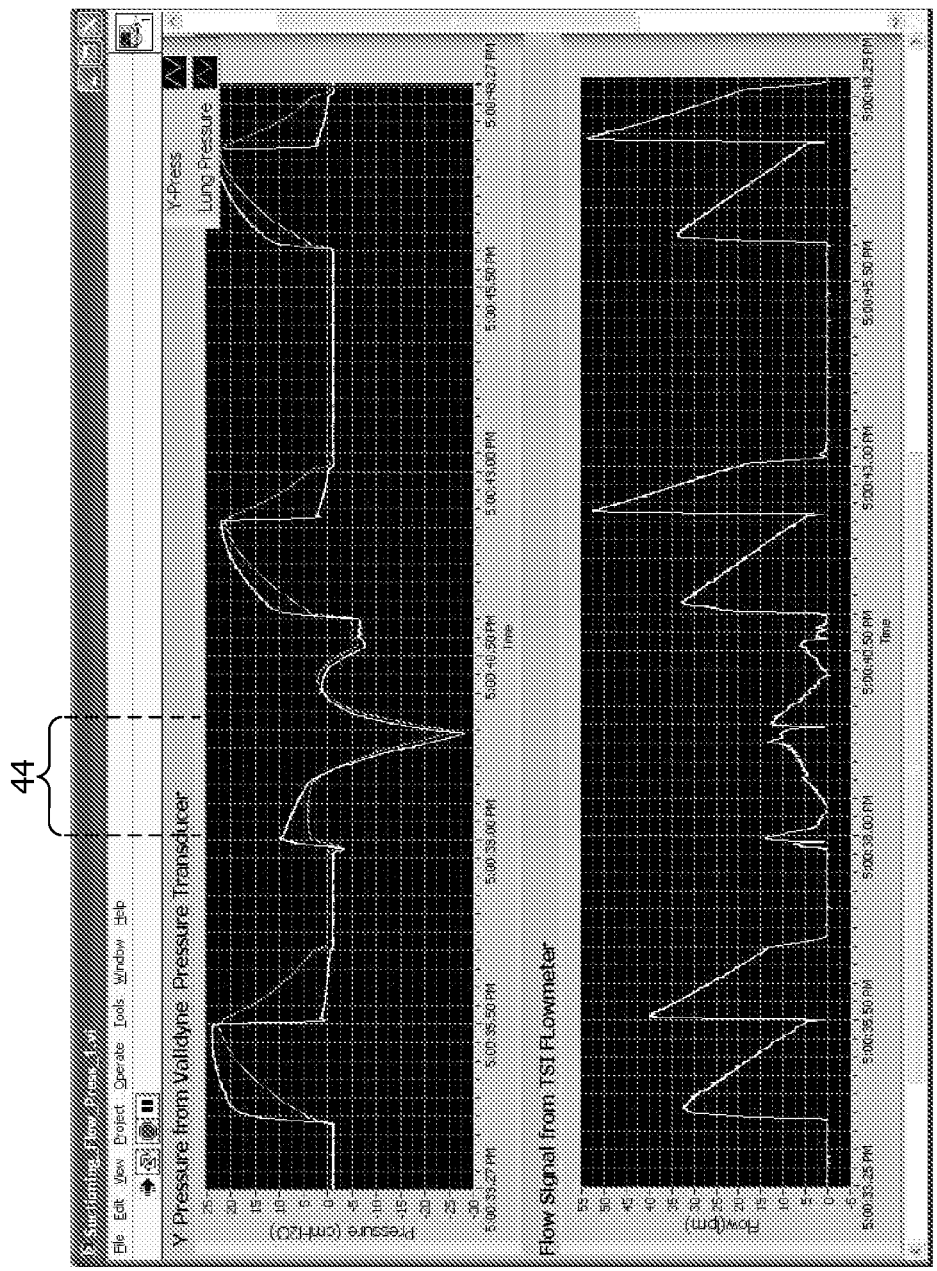
FIG. 2 illustrates plots of pressure and flow at or near the airway of a subject during secretion removal.

FIG. 2 shows plots of pressure and volume versus time at or near the airway of a subject being mechanically ventilated. For a period of time 42, suction is applied to the airway of the subject to remove secretions therefrom. The period of time 42 is relatively short, and takes place during expiration. As can be seen in FIG. 2, the application of suction during period of time 42 causes a substantial negative pressure at the airway of the subject.

Figure 3:
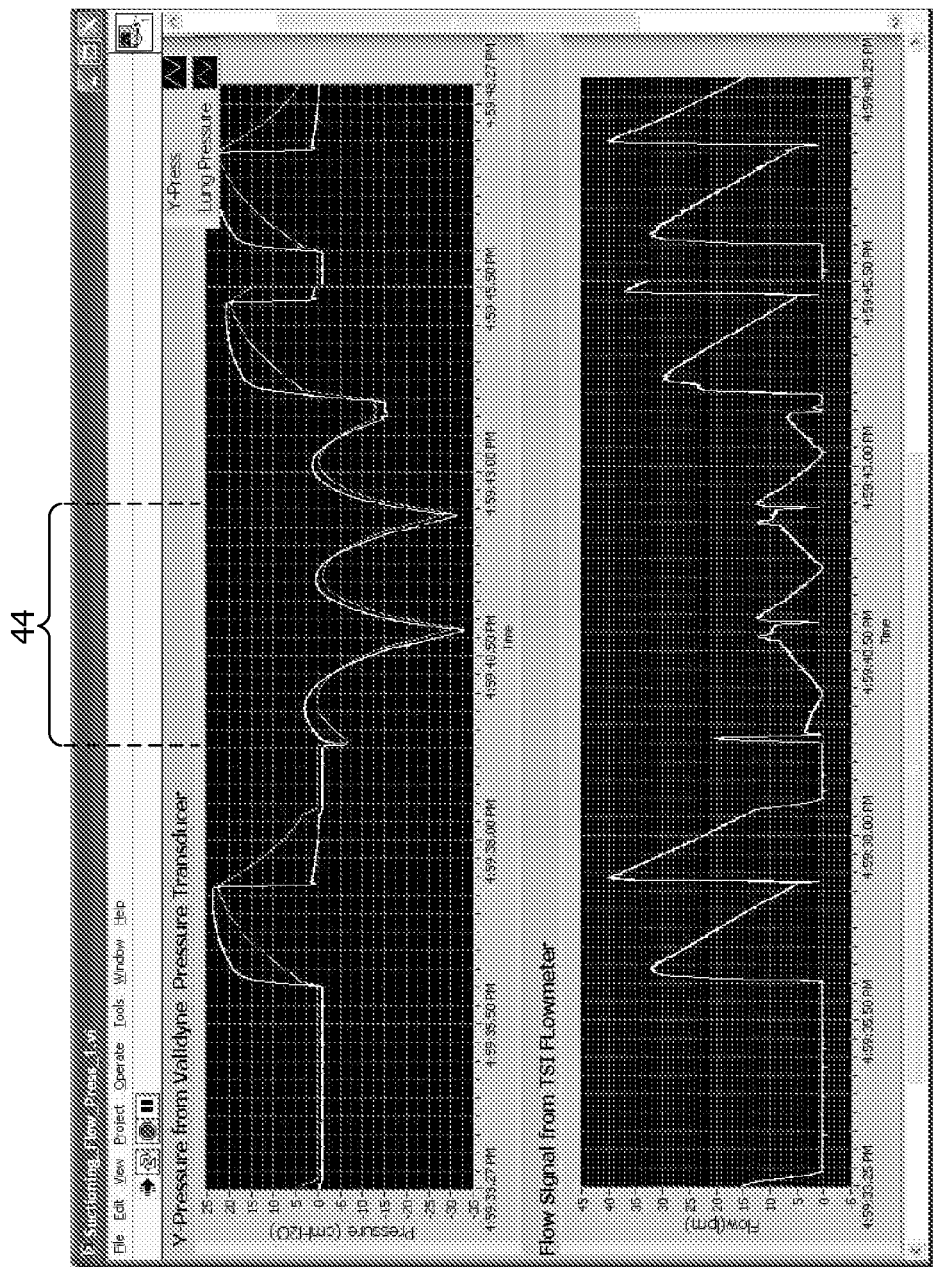
FIG. 3 illustrates plots of pressure and flow at or near the airway of a subject during secretion removal.

FIG. 3 shows a plot of pressure and volume versus time at or near the airway of a subject being mechanically ventilated. For a period of time 44, suction is applied to the airway of the subject to remove secretions therefrom. The period of time 44 is longer than the period of time 42 shown in FIG. 2 and described above, and results in a drop in pressure at the airway of the subject that is more extreme and more prolonged than the drop in pressure shown in FIG. 2. The ventilator triggering an cycling function is also compromised.

Figure 4:
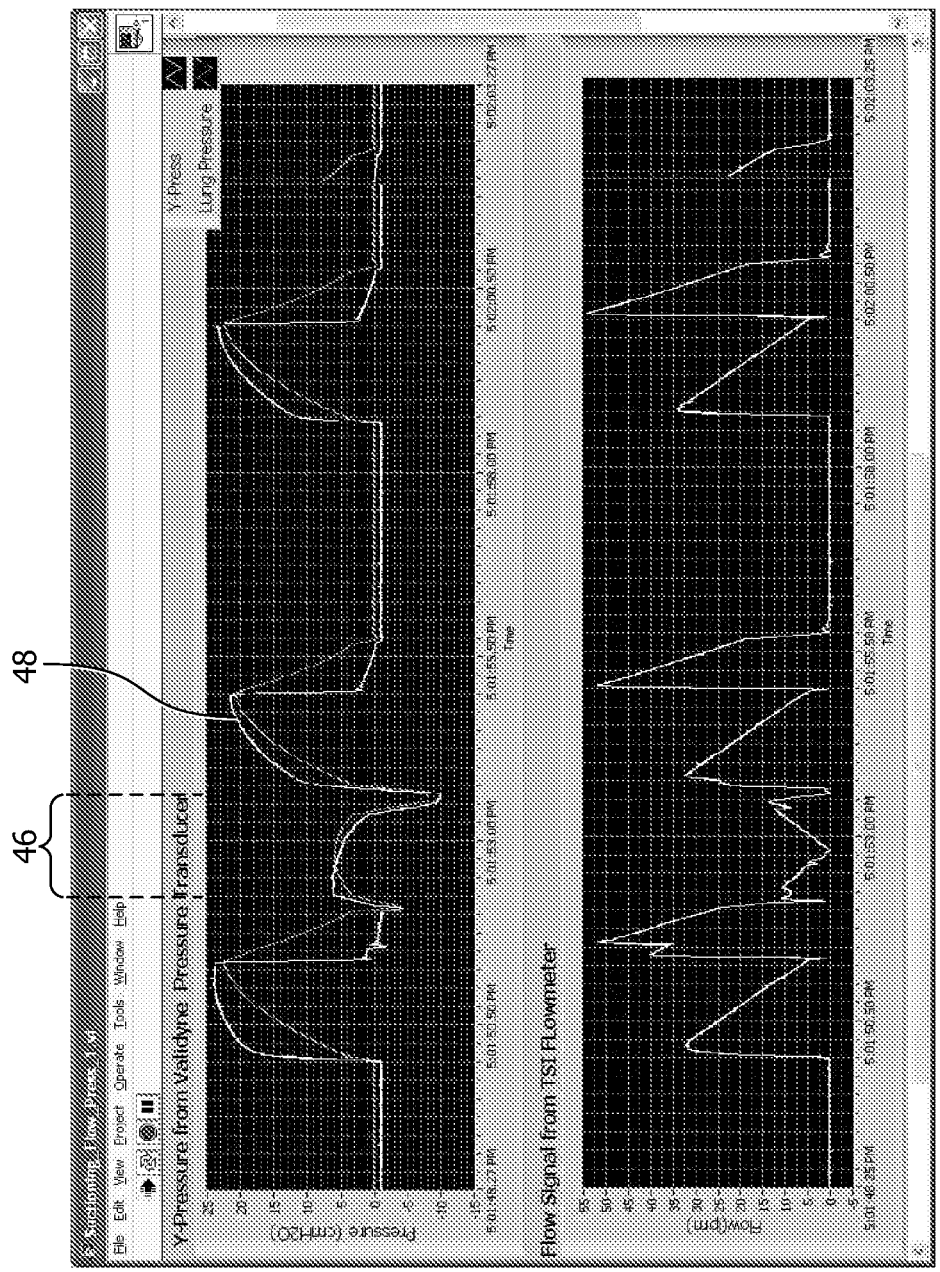
FIG. 4 illustrates plots of pressure and flow at or near the airway of a subject during secretion removal.

FIG. 4 shows plots of pressure and volume versus time at or near the airway of a subject being mechanically ventilated. For a period of time 46, suction is applied to the airway of the subject to remove secretions therefrom. As can be seen in FIG. 4, the period of time 46 is relatively early in expiration, and is relatively short in time. The result of these properties of period of time 46 is that the drop in pressure within the airway of the subject is lower than the drops in pressure accompanied with the applications of suction shown in FIGS. 2 and 3. As was discussed above, reducing this drop in pressure may mitigate the impact of secretion removal on the subject.

From the plots shown in FIG. 4, it can also be seen that to further mitigate the impact of secretion removal, period of time 46 is followed immediately by an inspiration 48. This inspiration may be executed by the system ventilating the subject based on the application of the suction during period of time 46, and may be out of rhythm with respect to the ventilation that was being conducted prior to the application of the suction.

Figure 5:
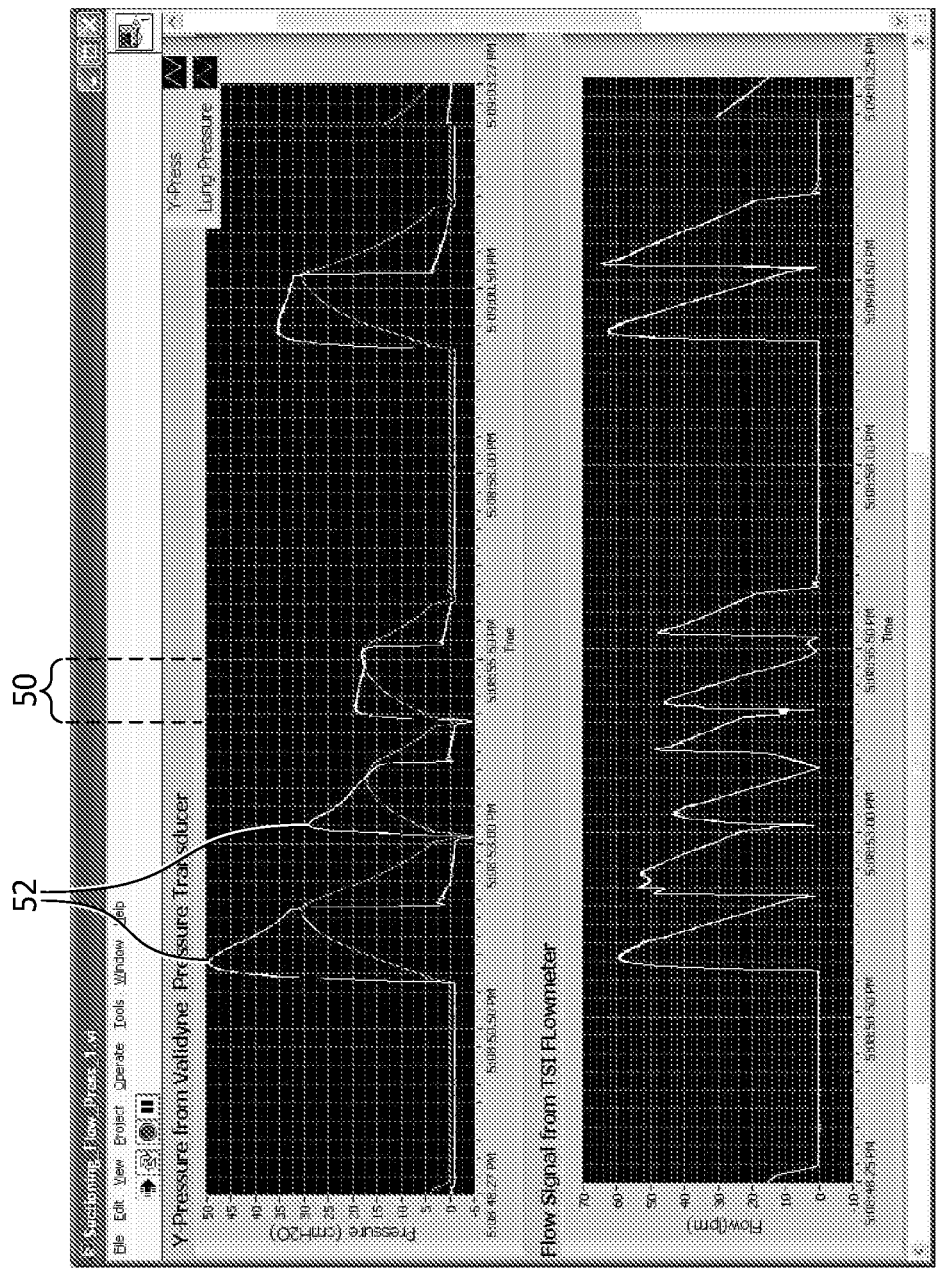
FIG. 5 illustrates plots of pressure and flow at or near the airway of a subject during secretion removal.

FIG. 5 shows plots of pressure and volume versus time at or near the airway of a subject being mechanically ventilated. For a period of time 50, suction is applied to the airway of the subject to remove secretions therefrom. As can be seen in FIG. 5, the period of time 50 begins at the end of inspiration, rather than during expiration (as was the case with FIGS. 2-4). This results in no substantial drop in lung pressure outside of the typical drop in pressure associated with inspiration. This may mitigate the impact of secretion removal on the subject.

In the plots shown in FIG. 5, it can further be observed that prior to the application of suction during period of time 50, a plurality of breaths 52 are stacked. The stacked breaths 52 may further mitigate the impact of secretion removal as a lung recruitment maneuver, and/or by oxygenating the lungs prior to the application of suction.

Returning to FIG. 1, flow generator control module 36 and suction timing module 38 may cooperate to implement the phenomena illustrated in FIGS. 2-5 to mitigate the impact of secretion removal. For example, flow generator control module 36 may control pressure generator 14 to stack breaths during the pre-suction sub-routine (e.g., as shown in FIG. 5), flow generator control module 36 may control pressure generator 14 to follow the application of suction with a breath or other lung recruitment maneuver during (e.g., as shown in FIG. 4), suction timing module 38 may generate a trigger signal to initiate suction at the end of inspiration (e.g., as shown in FIG. 5), suction timing module 38 may generate a trigger signal to manage the length of the period of time for which suction is applied to the airway, and/or flow generator control module 36 and/or suction timing module 38 may take other actions illustrated in FIGS. 2-5 and/or described herein to mitigate the impact of secretion removal.

The suction control module 40 is configured to control suction generator 32. In one embodiment, suction control module 40 controls suction generator 32 automatically in accordance with trigger signals generated by suction timing module 38.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilation system configured to generate a pressurized flow of breathable gas that is delivered to the airway of a subject to mechanically ventilate the subject, the ventilation system comprising:
   a pressure generator configured to generate a pressurized flow of breathable gas for delivery to an airway of a subject, the pressurized flow of breathable gas having one or more controllable gas parameters;
   one or more sensors configured to generate an output signal conveying information related to one or more gas parameters at or near the airway of the subject; and
   a processor configured to execute two or more computer program modules, the two or more computer program modules comprising at least:
   a suction timing module configured to generate a trigger signal indicating that suction through a suction catheter positioned at or near the airway of the subject to remove secretions should be initiated wherein the trigger signal is generated based on the output signal generated by the sensor; and
   a flow generator control module configured to control the pressure generator to facilitate removal of secretions from a flow path formed by an interface appliance and the airway of the subject during a secretion removal routine;
   wherein:
      the secretion removal routine includes a pre-suction sub-routine, a suction sub-routine, and a post-suction sub-routine for reducing the impact of a catheter-operated suction in a patient, the flow generator control module being configured to control the pressure generator to adjust the one or more controllable gas parameters during the pre-suction sub-routine, the suction sub-routine, and the post-suction sub-routine;
      during the pre-suction sub-routine, the humidity of the pressurized flow of breathable gas is elevated;
      during the suction sub-routine, suction is applied to the flow path to remove secretions;
      during the post-suction sub-routine, one or more of an elevated level of oxygen content in the pressurized flow of breathable gas and performance of lung recruitment maneuvers is provided;
      the processor is configured to: upon completion of the pre-suction subroutine, generate a cue to prompt a user to enter a control input; and
      the control input is configured to instruct the processor to proceed to the suction sub-routine.

2. The ventilation system of claim 1, wherein the computer program modules further comprise a suction control module configured to control suction through a suction catheter such that suction through the suction catheter is automatically initiated in response to the trigger signal generated by the suction timing module.

3. The ventilation system of claim 1, wherein the flow generator control module is configured to control the pressure generator to selectively adjust the one or more controllable gas parameters of the pressurized flow of breathable gas, to reduce variation in one or more gas parameters at or near the airway of the subject caused by suction through the suction catheter.

4. The ventilation system of claim 1, wherein the flow generator control module is configured to control the pressure generator to reduce variation in one or more of gas pressure, flow and volume at or near the airway of subject during the suction sub-routine.

5. The ventilation system of claim 1, wherein the flow generator control module is configured to adjust or switch ventilation modes to avoid a synchronized intermittent mandatory ventilation mode during the suction sub-routine.

6. The ventilation system of claim 1, wherein the two or more computer program modules further comprise a secretion detection module configured to determine a peak inspiratory pressure of the subject based on the output signal generated by the sensor, and wherein the secretion detection module is configured to generate a trigger signal indicating that the secretion removal routine should be initiated upon determination of said inspiratory peak.

7. The ventilation system of claim 1, wherein the two or more computer program modules further comprise a secretion detection module configured to determine a peak inspiratory pressure of the subject based on the output signal of the sensor, and wherein the secretion detection module is configured to detect secretions based on an increase in peak inspiratory pressure.

8. The ventilation system of claim 1, wherein during the pre-suction sub-routine, the oxygen content of the pressurized flow of breathable gas is elevated, the pressure and/or the flow of the pressurized flow of breathable gas is adjusted to insufflate the subject, or a positive end expiratory pressure is adjusted.

9. The ventilation system of claim 1, wherein during the post-suction sub-routine, an elevated level of oxygen content in the pressurized flow of breathable gas is provided.

10. The ventilation system of claim 1, wherein the one or more gas parameters include all of:
   flow rate;
   pressure;
   volume;
   humidity;
   temperature;
   gas composition;
   breath rate;
   tidal volume;
   peak flow;
   inhalation timing; and
   exhalation timing.

11. The ventilation system configured to generate a pressurized flow of breathable gas that is delivered to the airway of a subject to mechanically ventilate the subject, the ventilation system comprising:
   a pressure generator configured to generate a pressurized flow of breathable gas for delivery to an airway of a subject, the pressurized flow of breathable gas having one or more controllable gas parameters;
   one or more sensors configured to generate an output signal conveying information related to one or more gas parameters at or near the airway of the subject; and
   a processor configured to execute two or more computer program modules, the two or more computer program modules comprising at least:
   a suction timing module configured to generate a trigger signal indicating that suction through a suction catheter positioned at or near the airway of the subject to remove secretions should be initiated wherein the trigger signal is generated based on the output signal generated by the sensor; and
   a flow generator control module configured to control the pressure generator to facilitate removal of secretions from a flow path formed by an interface appliance and the airway of the subject during a secretion removal routine;
wherein:
the secretion removal routine includes a pre-suction sub-routine, a suction sub-routine, and a post-suction sub-routine for reducing the impact of a catheter-operated suction in a patient, the flow generator control module being configured to control the pressure generator to adjust the one or more controllable gas parameters during the pre-suction sub-routine, the suction sub-routine, and the post-suction sub-routine;
during the pre-suction sub-routine, the humidity of the pressurized flow of breathable gas is elevated;
during the suction sub-routine, suction is applied to the flow path to remove secretions;
during the post-suction sub-routine, one or more of an elevated level of oxygen content in the pressurized flow of breathable gas and performance of lung recruitment maneuvers is provided;
wherein the processor is configured to: upon completion of the suction subroutine, generate a cue to prompt a user to enter a control input; and
wherein the control input is configured to instruct the processor to proceed to the post-suction sub-routine.

12. The ventilation system of claim 11, wherein the computer program modules further comprise a suction control module configured to control suction through a suction catheter such that suction through the suction catheter is automatically initiated in response to the trigger signal generated by the suction timing module.

13. The ventilation system of claim 11, wherein the flow generator control module is configured to control the pressure generator to selectively adjust the one or more controllable gas parameters of the pressurized flow of breathable gas, to reduce variation in one or more gas parameters at or near the airway of the subject caused by suction through the suction catheter.

14. The ventilation system of claim 11, wherein the flow generator control module is configured to control the pressure generator to reduce variation in one or more of gas pressure, flow and volume at or near the airway of subject during the suction sub-routine.

15. The ventilation system of claim 11, wherein the flow generator control module is configured to adjust or switch ventilation modes to avoid a synchronized intermittent mandatory ventilation mode during the suction sub-routine.

16. The ventilation system of claim 11, wherein the two or more computer program modules further comprise a secretion detection module configured to determine a peak inspiratory pressure of the subject based on the output signal generated by the sensor, and wherein the secretion detection module is configured to generate a trigger signal indicating that the secretion removal routine should be initiated upon determination of said inspiratory peak.

17. The ventilation system of claim 11, wherein the two or more computer program modules further comprise a secretion detection module configured to determine a peak inspiratory pressure of the subject based on the output signal of the sensor, and wherein the secretion detection module is configured to detect secretions based on an increase in peak inspiratory pressure.

18. The ventilation system of claim 11, wherein during the post-suction sub-routine, an elevated level of oxygen content in the pressurized flow of breathable gas is provided.

* * * * *